(12) United States Patent
Chandra et al.

(10) Patent No.: US 10,568,563 B2
(45) Date of Patent: Feb. 25, 2020

(54) DEVICE FOR ESTIMATING ROUGHNESS AND SHINE OF HAIR

(71) Applicant: Conopco, Inc., Englewood Cliffs, NJ (US)

(72) Inventors: Lalitesh Chandra, Great Sutton (GB); Shirish Subhash Desale, Chinchwad (IN); Tomas Zbigniew Paoli, Liverpool (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

(21) Appl. No.: 15/579,680

(22) PCT Filed: Jun. 20, 2016

(86) PCT No.: PCT/EP2016/064194
§ 371 (c)(1),
(2) Date: Dec. 5, 2017

(87) PCT Pub. No.: WO2017/001229
PCT Pub. Date: Jan. 5, 2017

(65) Prior Publication Data
US 2018/0140248 A1   May 24, 2018

(30) Foreign Application Priority Data
Jun. 30, 2015  (EP) .................................. 15174430

(51) Int. Cl.
*A61B 5/00*  (2006.01)
*G01B 21/30*  (2006.01)
*A61B 5/103*  (2006.01)

(52) U.S. Cl.
CPC ............ *A61B 5/448* (2013.01); *A61B 5/1034* (2013.01); *G01B 21/30* (2013.01)

(58) Field of Classification Search
CPC ....................................................... A61B 5/448
(Continued)

(56) References Cited

U.S. PATENT DOCUMENTS

| 4,534,644 | A | * | 8/1985 | Beesley | .................... | G01J 3/52 |
| | | | | | | 356/30 |
| 5,236,365 | A | * | 8/1993 | Badami | .................. | G09B 25/00 |
| | | | | | | 132/294 |

(Continued)

FOREIGN PATENT DOCUMENTS

| CN | 2000185030 | 7/2000 |
| CN | 101743069 | 6/2010 |

(Continued)

OTHER PUBLICATIONS

Bergmann et al., Analysis of haptic perception of materials by multidimensional scaling and physical measurements of roughness and compressibility, ACTA Psychologica, Jan. 1, 2006, 1-20, vol. 121 No. 1.

(Continued)

*Primary Examiner* — Tarifur R Chowdhury
*Assistant Examiner* — Omar H Nixon
(74) *Attorney, Agent, or Firm* — Foley & Lardner LLP

(57) ABSTRACT

A device for measuring roughness and shine of hair, comprising a) a first area comprising an ascending gradient of shine, and b) a second area comprising an ascending gradient of roughness, wherein the first area is aligned to the second area, and wherein the ascending gradient of shine and the ascending gradient of texture are inverse to each other, and wherein the roughness is provided by a textured pattern which is textured to mimic hair.

18 Claims, 5 Drawing Sheets

(58) Field of Classification Search
USPC .......................................................... 356/421
See application file for complete search history.

(56) References Cited

U.S. PATENT DOCUMENTS

| | | | | |
|---|---|---|---|---|
| 5,311,293 | A * | 5/1994 | MacFarlane | A45D 44/005 356/421 |
| 5,692,900 | A | 12/1997 | Fischer | |
| 5,705,147 | A * | 1/1998 | Shapiro | A61K 8/361 424/70.1 |
| 6,000,407 | A * | 12/1999 | Galazin | A45D 44/005 132/200 |
| 6,338,349 | B1 * | 1/2002 | Robinson | A45D 40/24 132/200 |
| 2002/0140936 | A1 | 10/2002 | De Rigal et al. | |
| 2003/0224318 | A1 | 12/2003 | Weinstein | |
| 2003/0234650 | A1 | 12/2003 | Bron | |
| 2008/0153054 | A1 | 6/2008 | Masters et al. | |
| 2011/0117292 | A1 | 5/2011 | Wu et al. | |
| 2011/0229696 | A1 | 9/2011 | Ratnukumar et al. | |
| 2013/0142750 | A1 * | 6/2013 | Fair | A61Q 5/00 424/70.122 |

FOREIGN PATENT DOCUMENTS

| | | |
|---|---|---|
| CN | 102160092 | 8/2011 |
| CN | 103063617 | 4/2013 |
| JP | 2004195722 | 7/2004 |
| WO | WO2014170108 | 10/2014 |

OTHER PUBLICATIONS

Brenda Barrett, How to tell if your hair is damaged, Black Hair Media Internet, Apr. 13, 2012, XP002698004.
Reimer et al., An Objective Method for Evaluating Hair Shine, Soap Cosmetcs Chemical Specialties, Oct. 1, 1995, pp. 44-47, v. 71, No. 10.
Zemetrics, Surface roughness measurement concerns, Zemetrics Surface Measurment, Feb. 6, 2012.
Search Report & Written Opinion in PCTEP2016064194, dated Sep. 19, 2016.
Search Report and Written Opinion in EP15174430, dated Dec. 7, 2017.
Written Opinion in PCTEP2016064194, dated May 11, 2017.
IPRP2 in PCTEP2016064194, dated Sep. 5, 2017.
Takeshi Okuyama, et al., Development of tactile sensor for measuring hair touch feeling, Microsyst .Technol., 2011, pp. 1153-1160, 17.

* cited by examiner

DEVICE FOR ESTIMATING ROUGHNESS AND SHINE OF HAIR

FIELD OF THE INVENTION

The present invention relates to a device for measuring roughness and shine of hair.

BACKGROUND AND PRIOR ART

Many modern hair products are tailored to provide benefits to specific properties of hair, such as fineness, curliness, dryness, greasiness, level of damage, and so on. For a consumer to choose the right hair products, he/she must have knowledge of the condition of their hair. In order to achieve this knowledge, it is advantageous to carry out an assessment of the hair.

Methods of measuring roughness and other properties of surfaces are described in the following prior art.

US 2003/0234650 discloses a comparator for surface finishes for the evaluation of SPI surface finishes with the turbine steam path. An embodiment comprises a small particle impingement comparator comprising a plurality of sample cells arranged side-by-side in ascending order of roughness from 1190 micro-inches to 6950 micro-inches.

Microsyst Tecnol (2011) 17:1153-1160, describes a sensor system for the evaluation of hair, under dry and wet conditions. The sensor consists of an acrylic base, a silicone runner and a polyvinylidene fluoride film. A surface projection is put on the PVDF film. It is used to measure a range of hair feel properties including roughness, slippery-smooth, smooth, squeak and moist.

Our co-pending patent application, PCT/EP2014/056104 discloses a self-assessment device comprising a series of rough patches of increasing roughness and which may be contacted by user and compared with the roughness of a hair sample in order to provide an indication to the user as to the relative state of the hair sample.

US2002/0140936 discloses a system comprising a plurality of comparison samples configured to substantially simulate the appearance of a keratinous element. Each comparison sample may be configured to substantially simulate both a colour and an appearance characteristic other than colour of the keratinous element.

Despite the prior art there remains a need for improved devices that provide accurate yet simple means for assessing the state of hair fibres and for devices that enable more than one property of hair to be measured simultaneously. The prior art only provides devices where properties are measured using a single sensory aspect, namely touch or appearance. We have now found that by combining the use of the different sensory aspects of feel and appearance, a more useful and insightful assessment is made. We have found that by aligning two scales of properties pertaining to the two different aspects, roughness and shine, the relationship between them is indicated to the user, thus enabling insight as well as more suitable, targeted treatment regimes to be recommended.

Definition of the Invention

Accordingly, in a first aspect of the invention, there is provided a device for measuring roughness and shine of hair, comprising:
a) a first area comprising an ascending gradient of shine, and
b) a second area comprising an ascending gradient of roughness,
wherein the first area is aligned to the second area,
and wherein the ascending gradient of shine and the ascending gradient of texture are inverse to each other,
and wherein the roughness is provided by a textured pattern which is textured to mimic hair.

In a second aspect there is provided a method for assessing the state of hair, using the device of the first aspect of the invention, comprising the steps of:
a) contacting a hair sample,
b) contacting a gradient of roughness on the device,
c) bending the hair sample to create a shine halo and visually comparing the shine halo with the shine gradient on the device according on the first aspect,
d) optionally repeating one or more of steps A), B) and C), and
e) concluding which position on the gradient of roughness and which position on the gradient of shine has the most similar roughness and shine to the hair sample.

In a third aspect there is provided a kit comprising a hair care composition and a device in accordance with the first aspect of the invention.

In a fourth aspect there is provided a package for a hair care composition comprising a device as described above.

The inverse nature of the ascending gradient of shine and the ascending gradient of texture is intended to indicate a typical relationship between the two properties. Hair that is rough often bears less shine than smooth, healthy hair. However, depending on the individual nature of damage sustained by an individual's hair, the relationship between the two properties can become skewed. For example, some hair damaged by bleach treatments can exhibit a low shine whereas some swimmers notice that their hair becomes more shiny, although both are rougher. Therefore, the present invention highlights any diversion from the usual relationship between roughness and shine, and enables targeted treatments to be recommended, for example a treatment to target the roughness, or a treatment (or treatments) to target the roughness and the shine.

One or more of the following preferred additional steps may be included in the method of the invention:—

The method may further comprise making a product recommendation based on the conclusion generated by the self-assessment. For example, should the assessor judge that the hair is damaged then the recommendation might be to recommend a composition suitable for damage repair. Alternatively, the levels of treatment for shine and roughness may be individually recommended.

The method may further comprise making an overall assessment of the state of the hair by combining the position of roughness and the position of shine.

DETAILED DESCRIPTION OF THE INVENTION

The First Area

The first area comprises an ascending gradient of shine.

The ascending gradient of shine may be made up of a plurality of samples cells, wherein the sample cells have different levels of shine and are arranged side-by-side in ascending order of increasing shine.

Alternatively, the ascending gradient of shine may be continuous.

Shine of hair is typically measured manually or by using a suitable instrument.

Preferably, the first area of the device in accordance with the invention is calibrated against consumer perception and/or instrumental measurement of shine.

A suitable method of measuring shine of hair instrumentally, is as follows. Shine of hair may be measured using a shinometer (for example a Black and White SAMBA) which comprises a root holder, a tress holder and a camera. A switch of hair is typically employed.

1) The root end of a switch of hair is positioned in the root holder.
2) The switch is allowed to fall naturally over the tress holder maintaining the natural fall.
3) The tress holder and hair switch are placed under the camera.
4) A screen, such as a curtain, is placed to prevent any excess light interfering with the measurement.
5) A shine measurement is taken using Hair Visualisation Appearance Software (HVAS).

Consumers and professionals (for example in a salon environment) typically measure shine using manual assessment methods.

Typically, a manual shine measurement comprises a visual assessment of how well hair reflects light. Artificial or natural light may be used, or a combination thereof. Preferably, natural light is used. The assessment is preferably carried out on clean hair.

A suitable method for making a manual shine assessment in accordance with the invention is as follows:

A bundle of hair is held in a bent or curved configuration to create a sharp line of light transversely across the bundle of hair (herein referred to as a "shine halo").

This can then be compared with the shine gradient on the device.

The sharper the shine halo, the higher the shine.

Where the device is flexible, preferably the device is also held in a bent or curved configuration during the comparison. The hair and/or device may be bent and held over a curved surface, for example a finger, head, brush or barrel.

A suitable method of measuring shine using the device of the invention is as follows:

A section of hair, preferably about an inch wide, is selected.

A device in accordance with the invention is held along the length of the section of hair. Preferably, the shiniest end of the gradient of shine is held at the root and the least shiniest towards the ends of the hair section.

An overall assessment of the shine level is made by determining the position on the gradient of shine that most closely matches the shine level of the hair.

An alternative method is as follows:

A device in accordance with the invention is held diagonally about 2 inches from the root of the hair.

The device is bent, for example around the curve of the head.

An assessment of the shine level is made by determining the position on the gradient of shine that most closely match the shine level of the hair.

The Second Area

The second area comprises an ascending gradient of roughness.

The ascending gradient of roughness may be made up of a plurality of samples cells, wherein the sample cells have different levels of roughness and are arranged side-by-side in ascending order of increasing roughness.

Alternatively, the ascending gradient of roughness may be continuous.

The roughness is provided by a textured pattern. The textured pattern is textured to mimic hair. The textured pattern can comprise at least one of the texture elements and material properties in the following description:—

Surface texture has elements of lay (the machining or forming pattern), surface roughness, and waviness. In addition, inherent material properties may contribute to surface porosity, inclusions, and residual elements.

The parameters of texture are vertical amplitude variations, horizontal spacing variations, or some hybrid combination of these.

Surface roughness is an expression of finely spaced vertical surface irregularities, as opposed to waviness, which is irregularities with spacing greater than surface roughness. Surface roughness is provided by the presence of vertical surface irregularities or friction providing means.

Preferably the surface irregularities are in the form of raised or depressed features. Such features may be regularly or irregularly shaped and may be regularly or irregularly presented.

In the device of the invention, the texture elements are designed to mimic hair. The roughness increases from one end of the device to the other. This is intended to mimic the increase in roughness from the root of hair to the tip.

Preferably, the device has an area of 15 to 150 $cm^2$, more preferably 30 to 125 $cm^2$, most preferably 80 to 129 $cm^2$. Preferably the ration of length:width is 3 to 9:1, more preferably 4 to 6:1 and most preferably 5 to 6:1.

The Device

The device preferably comprises a base material, preferably plastic, cardboard or both. The device is preferably flexible. This enables the device to be held in a bent or curved configuration during the methods of the invention.

The shine area and the textured area are preferably transposed onto each other. In this case, it is easier to see which combined shine and texture the hair most resembles, rather than having shine and texture readings at different points on the scale. Thus, an overall damage or state assessment can be more easily determined.

The device preferably further comprises a scale. The scale may indicate the level the roughness, or shine, or be indicative of both.

Preferably, an image of hair fibres is transposed onto the textured pattern.

Kit Comprising the Device

A kit may be provided, comprising a hair care composition and a device in accordance with the first aspect of the invention. Preferably, the kit further comprises instructions to the method of the invention.

Preferably, the hair care composition is selected from shampoos, rinse-off conditioners, leave-on conditioners, overnight treatments, mousses, gels and styling compositions.

Preferably, the composition is a conditioning composition whether a shampoo conditioner 2-in-1 composition or a dedicated conditioning composition which is to be used subsequent to hair cleansing.

Preferably, the composition comprises a conditioning active. Preferably the composition comprises a shine enhancing active.

The composition according to the second aspect of the invention are preferably leave-on or rinse-off conditioning compositions. By conditioning composition is meant compositions which have as their primary object conditioning keratinous fibre, such as hair, as opposed to compositions which have as their primary aim cleansing the hair while providing a conditioning benefit. Accordingly, it is preferred that the composition comprises less than 5% wt. anionic surfactant, more preferably less than 5% wt. cleansing surfactant. More preferably, the composition comprises less than 3% wt. anionic surfactant, still more preferably less than 3% wt. cleansing surfactant and especially preferably no anionic surfactant.

A preferred conditioner comprises a conditioning gel phase. Such conditioners and methods for making them are described in WO2014/016354, WO2014/016353, WO2012/016352 and WO2014/016351.

By leave-on composition is meant that the composition is applied to the hair and not rinsed-off. Typically, this is applied to the hair before the user goes to bed at night.

The composition according to the invention comprises from 0.001 to 5% wt. conditioning active, more preferably from 0.1 to 4.0% by wt. conditioning active.

Preferably, the composition comprises a conditioning active selected from acid neutralized amidoamine surfactant, fatty alcohols and conditioning silicones. Preferably, the acid neutralized amidoamine surfactant is of general formula:

R1-C(O)—NH—R2-N(R3)(R4)

wherein R1 is a fatty acid chain with from 12 to 22 carbon atoms, R2 is an alkylene group containing from one to 4 carbon atoms and R3 and R4 are, independently, an alkyl group having from one to four carbon atoms.

Preferably, the acid neutralized amidoamine surfactant is selected from stearamidopropyl dimethylamine, stearamidopropyl diethylamine, stearamidoethyl dimethylamine, stearamidoethyl diethylamine, palimtamidopropyl dimethylamine, behenamidopropyl dimethylamine, myristamidopropyl dimethylamine, oleoamidopropyl dimethylamine, ricinoleoamidopropyl dimethylamine and mixtures.

Preferably, the composition according to the invention comprises less than 0.5% wt. cationic surfactant. More preferably, the composition according to the invention comprises less than 0.2% wt. cationic surfactant.

Preferably, the composition according to the invention comprises less than 0.5% wt. and more preferably less than 0.2% wt. a cationic surfactant selected from cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quatemium-18.

Conditioners of the invention advantageously incorporate a fatty alcohol material. The combined use of fatty alcohol materials and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol material in conditioners of the invention is conveniently from 0.01 to 5%, preferably from 0.1 to 3% by weight of the composition.

Silicone is a particularly preferred ingredient in hair treatment compositions of the invention. In particular, conditioners of the invention will preferably also comprise emulsified particles of silicone, for enhancing conditioning performance. The silicone is insoluble in the aqueous matrix of the composition and so is present in an emulsified form, with the silicone present as dispersed particles.

Suitable silicones include polydiorganosiloxanes, in particular polydimethylsiloxanes which have the CTFA designation dimethicone. Also suitable for use compositions of the invention are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning.

The viscosity of the emulsified silicone itself (not the emulsion or the final hair conditioning composition) is typically at least 10,000 cst. In general we have found that conditioning performance increases with increased viscosity. Accordingly, the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in conditioners of the invention will typically have an average silicone particle size in the composition of less than 30, preferably less than 20, more preferably less than 10 microns. We have found that reducing the particle size generally improves conditioning performance. Most preferably the average silicone particle size of the emulsified silicone in the composition is less than 2 microns, ideally it ranges from 0.01 to 1 micron. Silicone emulsions having an average silicone particle size of 0.15 microns are generally termed microemulsions.

Particle size may be measured by means of a laser light scattering technique, using a 2600D Particle Sizer from Malvern Instruments.

Suitable silicone emulsions for use in the invention are also commercially available in a pre-emulsified form.

Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

A further preferred class of silicones for inclusion in conditioners of the invention are amino functional silicones. By "amino functional silicone" is meant a silicone containing at least one primary, secondary or tertiary amine group, or a quaternary ammonium group. Examples of suitable amino functional silicones include:

(i) polysiloxanes having the CTFA designation "amodimethicone", and the general formula:

HO—[Si(CH$_3$)$_2$—O—]$_x$—[Si(OH)(CH$_2$CH$_2$CH$_2$—NH—CH$_2$CH$_2$NH$_2$)—O—]$_y$—H in which x and y are numbers depending on the molecular weight of the polymer, generally such that the molecular weight is between about 5,000 and 500,000.

(ii) polysiloxanes having the general formula:

R'$_a$G$_{3-a}$-Si(OSiG$_2$)$_n$-(OSiG$_b$R'$_{2-b}$)$_m$—O—SiG$_{3-a}$-R'$_a$ in which:
G is selected from H, phenyl, OH or $C_{1-8}$ alkyl, e.g. methyl;
a is 0 or an integer from 1 to 3, preferably 0;
b is 0 or 1, preferably 1;
m and n are numbers such that (m+n) can range from 1 to 2000, preferably from 50 to 150;
m is a number from 1 to 2000, preferably from 1 to 10;
n is a number from 0 to 1999, preferably from 49 to 149, and R' is a monovalent radical of formula $-C_qH_{2q}L$ in which q is a number from 2 to 8 and L is an aminofunctional group selected from the following:

—NR"—$CH_2$—$CH_2$—N(R")$_2$
—N(R")$_2$
—N$^+$(R")$_3$A$^-$
—N$^+$H(R")$_2$A$^-$
—N$^+$H$_2$(R")A$^-$
—N(R")—$CH_2$—$CH_2$—N$^+$H$_2$(R")A$^-$ in which R" is selected from H, phenyl, benzyl, or a saturated monovalent hydrocarbon radical, e.g. $C_{1-20}$ alkyl, and;

A is a halide ion, e.g. chloride or bromide.

Suitable amino functional silicones corresponding to the above formula include those polysiloxanes termed "trimethylsilylamodimethicone" as depicted below, and which are sufficiently water insoluble so as to be useful in compositions of the invention:

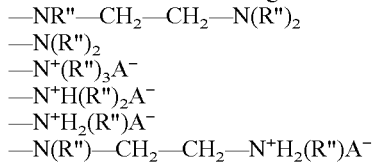

wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula:

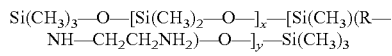

wherein $R^1$ and $R^{10}$ may be the same or different and may be independently selected from H, saturated or unsaturated long or short chain alk(en)yl, branched chain alk(en)yl and $C_5$-$C_8$ cyclic ring systems;
$R^2$ thru' $R^9$ may be the same or different and may be independently selected from H, straight or branched chain lower alk(en)yl, and $C_5$-$C_8$ cyclic ring systems;
n is a number within the range of about 60 to about 120, preferably about 80, and $X^-$ is preferably acetate, but may instead be for example halide, organic carboxylate, organic sulphonate or the like.

Suitable quaternary silicone polymers of this class are described in EP-A-0 530 974. Amino functional silicones suitable for use in compositions of the invention will typically have a mole % amine functionality in the range of from about 0.1 to about 8.0 mole %, preferably from about 0.1 to about 5.0 mole %, most preferably from about 0.1 to about 2.0 mole %. In general the amine concentration should not exceed about 8.0 mole % since we have found that too high an amine concentration can be detrimental to total silicone deposition and therefore conditioning performance.

The viscosity of the amino functional silicone is not particularly critical and can suitably range from about 100 to about 500,000 cst.

Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

Also suitable are emulsions of amino functional silicone oils with non ionic and/or cationic surfactant.

Suitably such pre-formed emulsions will have an average amino functional silicone particle size in the composition of less than 30, preferably less than 20, more preferably less than 10 microns. Again, we have found that reducing the particle size generally improves conditioning performance. Most preferably the average amino functional silicone particle size in the composition is less than 2 microns, ideally it ranges from 0.01 to 1 micron. Silicone emulsions having an average silicone particle size of ≤0.15 microns are generally termed microemulsions.

Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning).

An example of a quaternary silicone polymer useful in the present invention is the material K3474, ex Goldschmidt.

The total amount of silicone incorporated into compositions of the invention depends on the level of conditioning desired and the material used. A preferred amount is from 0.01 to about 5% by weight of the total composition although these limits are not absolute. The lower limit is determined by the minimum level to achieve conditioning and the upper limit by the maximum level to avoid making the hair and/or skin unacceptably greasy. Preferably, the composition comprises from 0.3 to 4%, preferably 0.5 to 3%, by weight of the total composition is a suitable level.

In a fourth aspect there is provided a package for a hair care composition comprising a device as described above.

Preferably, the package is a squeezable container such as a bottle or tottle and contains a product selected from shampoos, rinse-off conditioners, leave-on conditioners, overnight treatments, mousses, gels and styling compositions.

Preferably, the package is secondary packing for a squeezable container. Such secondary packaging is typically a carton or blister pack and the device may be part of the carton or blister pack.

Preferably, the device is detachable from said package. This improves engagement with the consumer since they are immediately actively engaged with the device.

Suitably the device may be stuck on or directly printed onto the bottle or package. Embodiments of the invention will now be described with reference to the following non-limiting drawings in which.

Figure 1:
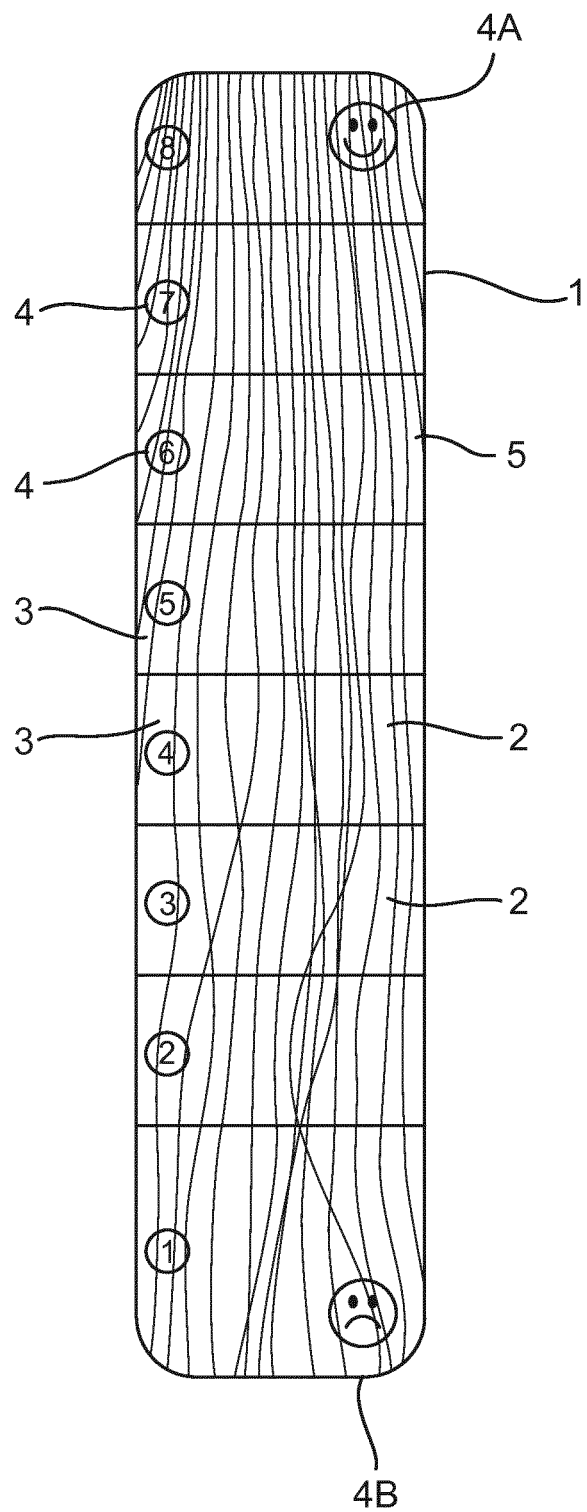
FIG. 1 is a perspective view of a device in accordance with the invention.

In detail, FIG. 1 shows a device (1) with an ascending gradient of roughness (2) and an ascending gradient of shine (3), which are inverse to each other and transposed onto each other. Indicators (4) indicate to the assessor the roughness and shine at each position. Indicators (4A) and (4B) are caricatures indicating a low roughness and high shine (4A) or a high roughness and low shine (4B) result. An image of hair fibres (5) is transposed onto the device.

Figure 2:
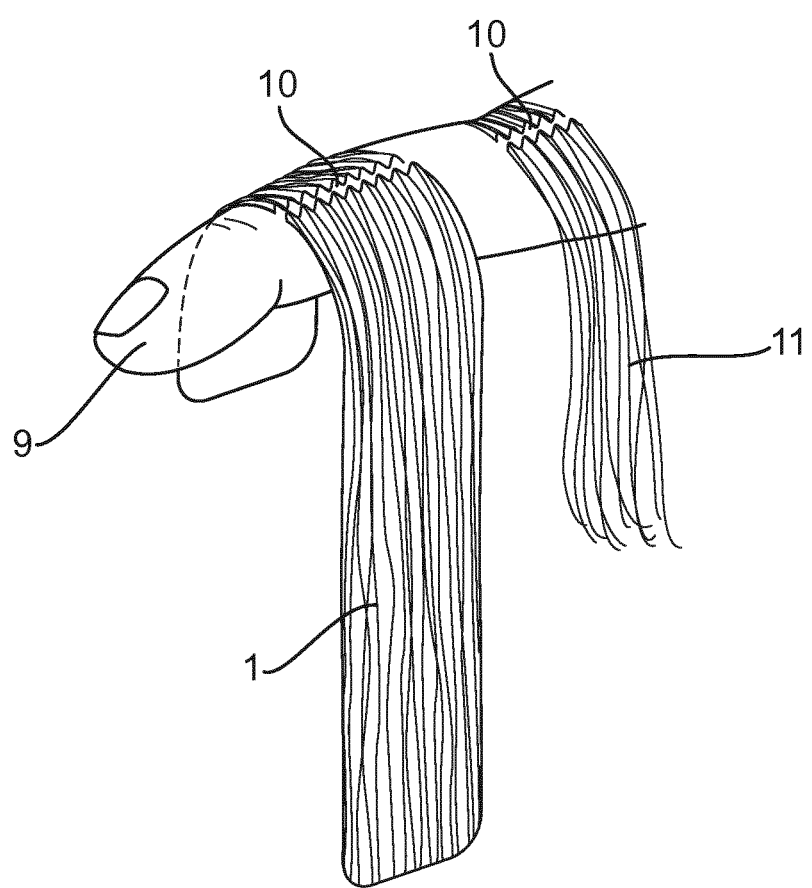
FIG. 2 is a perspective view of a device in use.

In FIG. 2, the device (1) is bent over the assessor's finger (9) to create a shine halo (10) next to a bundle of hair fibres (11) which are similarly bent over the finger (9) to create a shine halo (10). In this way a comparison between the shine of the hair fibres and the position of the shine gradient on the device may be carried out.

Figure 3:
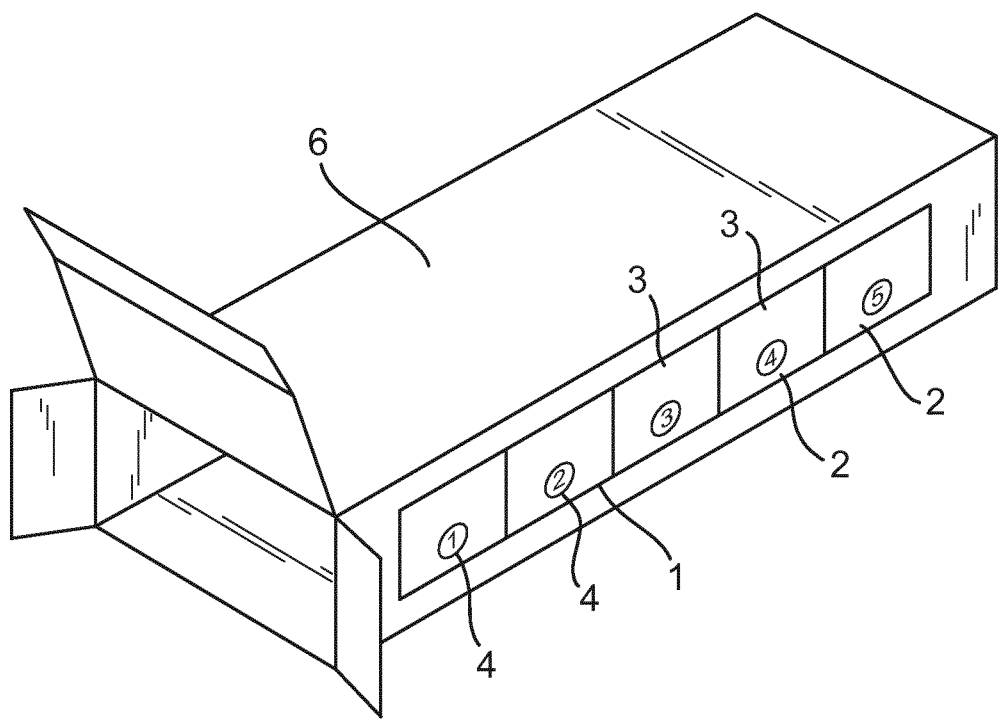
FIG. 3 is a perspective view of a device as part of secondary packaging.

FIG. 3 shows a secondary package (6) for a hair treatment composition which comprises a device (1) on its side wall. The device (1) has an ascending gradient of roughness (2) and an ascending gradient of shine (3), which are inverse to each other and transposed onto each other, which are marked (4) to indicate the roughness and shine and thus the state of the hair sample being assessed.

Figure 4:
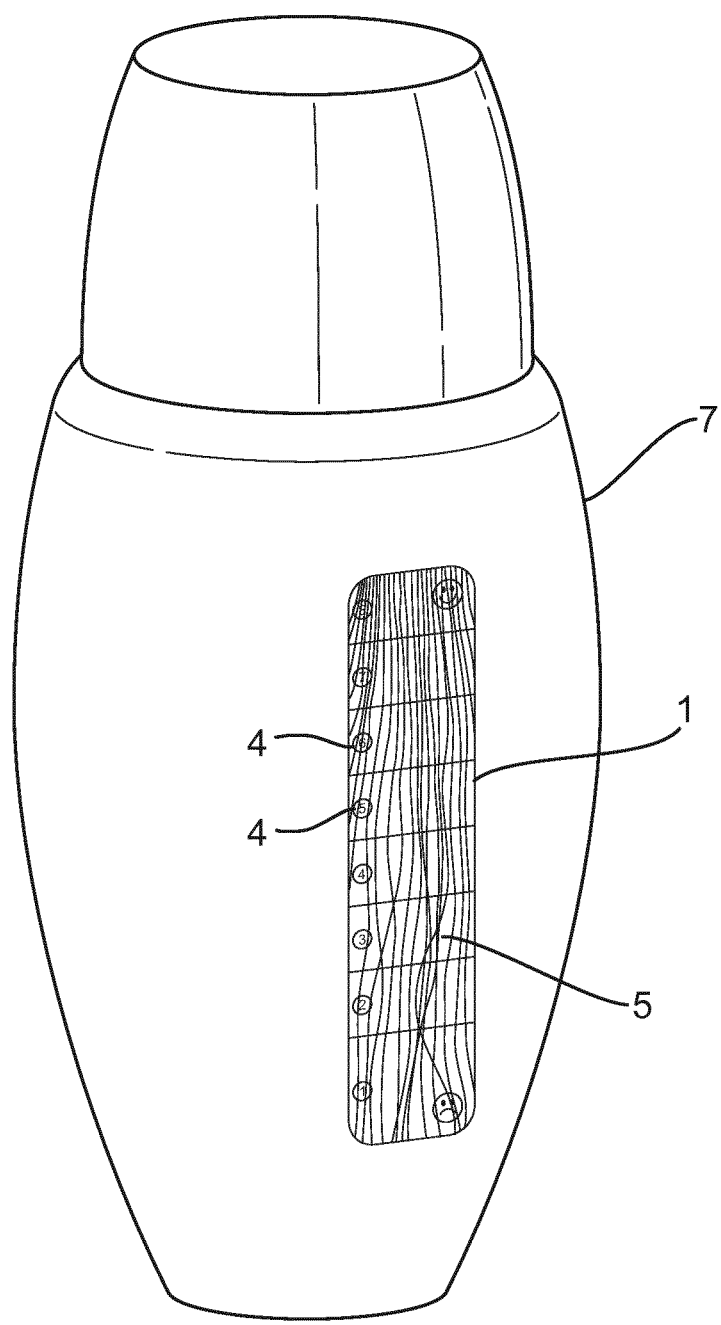
FIG. 4 is a side view of a device as part of a bottle for a hair treatment composition.

FIG. 4 shows a bottle (7) with a device (1) as part of its external wall.

Figure 5:
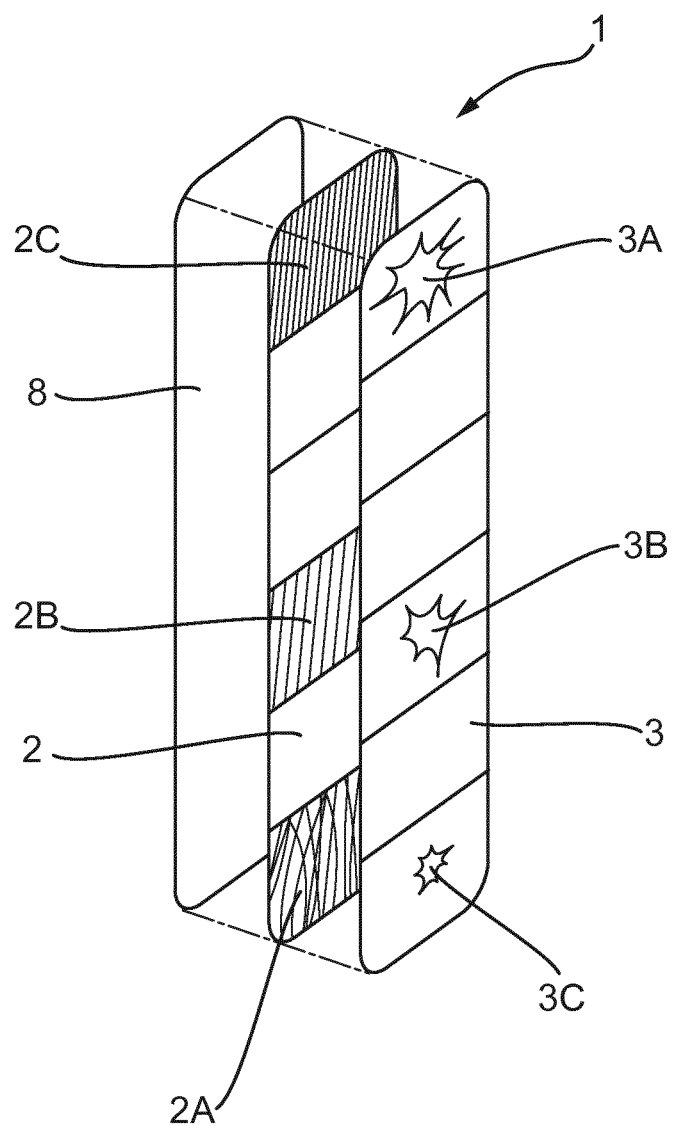
FIG. 5 is an expanded view of a device.

FIG. 5 shows an expanded view of a device (1) showing a first area comprising an ascending gradient of shine (3) and a second area comprising an ascending gradient of roughness (2). 3A indicates a high shine position, 3B an intermediate shine position and 3C a low shine position. 2A indicates a high roughness position, 2B an intermediate roughness position and 2C a low roughness position. A flexible backing (8) is also shown, upon which the first area (3) and second area (2) are transposed.

The invention claimed is:

1. A device for measuring roughness and shine of hair, the device comprising:
   a first area comprising an ascending gradient of shine, and
   a second area comprising an ascending gradient of roughness,
   wherein the first area is aligned to the second area,
   wherein the ascending gradient of shine and the ascending gradient of texture are inverse to each other, and
   wherein the roughness is provided by a textured pattern which is textured to mimic hair, and
   wherein the shine area and the textured area are transposed onto each other in the first area and the second area.

2. The device of claim 1, wherein an image of hair fibres is transposed onto the textured pattern.

3. The device of claim 1, further comprising a scale.

4. The device of claim 1, which is flexible.

5. The device of claim 1, further comprising a base material.

6. The device of claim 1, wherein the ascending gradient of shine is made up of a plurality of samples cells, wherein the sample cells have different levels of shine and are arranged side-by-side in ascending order of increasing shine.

7. The device of claim 1, wherein the ascending gradient of roughness is made up of a plurality of samples cells, wherein the sample cells have different levels of roughness and are arranged side-by-side in ascending order of increasing roughness.

8. A method for assessing the state of hair, using the device of claim 1, the method comprising the steps of:
   a) contacting a hair sample,
   b) contacting the gradient of roughness on the device,
   c) bending the hair sample to create a shine halo and visually comparing the shine halo with the shine gradient on the device according on the first aspect,
   d) optionally repeating one or more of steps a), b) and c), and
   e) concluding which position on the gradient of roughness and which position on the gradient of shine has the most similar roughness and shine to the hair sample.

9. A kit comprising a hair care composition and the device of claim 1.

10. The kit of claim 9, wherein the hair care composition comprises a fibre active or a conditioning active.

11. A package for a hair care composition comprising the device of claim 1.

12. The package of claim 11, wherein the package is a squeezable container.

13. The package of claim 11, which is secondary packing for a squeezable container.

14. The package of claim 11, wherein the device is detachable from the package.

15. A device for measuring hair characteristics, the device comprising:
   a backing;
   a plurality of textured portions arranged on the backing, each of the plurality of textured portions having a texture different from the others of the plurality of textured portions; and
   a plurality of icons, each of the plurality of icons disposed on one of the plurality of textured portions such that one of the plurality of icons is disposed on each of the plurality of textured portions.

16. The device of claim 15, wherein the textured portions are arranged according to the textures and each of the icons corresponds with one of the textures.

17. The device of claim 15, wherein the icons comprise at least one of a number or a caricature.

18. The device of claim 15, wherein:
   each of the icons has a size that is different from the others of the icons; and
   the icons are arranged according to the sizes.

* * * * *